(12) United States Patent
Janowski et al.

(10) Patent No.: US 8,114,160 B2
(45) Date of Patent: Feb. 14, 2012

(54) IMPLANT RETENTION DEVICE AND METHOD

(75) Inventors: Brian P. Janowski, Marquette, MI (US); Qi-Bin Bao, Marquette, MI (US); Thomas S. Kilpela, Marquette, MI (US); Jeffrey L. Trudeau, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 137 days.

(21) Appl. No.: 11/963,496

(22) Filed: Dec. 21, 2007

(65) Prior Publication Data

US 2008/0154263 A1 Jun. 26, 2008

Related U.S. Application Data

(60) Provisional application No. 60/871,641, filed on Dec. 22, 2006, provisional application No. 60/948,273, filed on Jul. 6, 2007.

(51) Int. Cl.
*A61F 2/44* (2006.01)

(52) U.S. Cl. .................................. 623/17.14; 623/17.13

(58) Field of Classification Search ..... 623/17.11–17.16
See application file for complete search history.

(56) References Cited

U.S. PATENT DOCUMENTS

| | | | |
|---|---|---|---|
| 3,875,595 A | 4/1975 | Froning | |
| 5,674,295 A * | 10/1997 | Ray et al. | 623/17.12 |
| 6,733,531 B1 * | 5/2004 | Trieu | 623/17.11 |
| 6,966,931 B2 | 11/2005 | Huang | |
| 7,033,393 B2 * | 4/2006 | Gainor et al. | 623/17.11 |
| 7,338,525 B2 | 3/2008 | Ferree | |
| 7,445,634 B2 * | 11/2008 | Trieu | 623/17.11 |
| 7,500,978 B2 * | 3/2009 | Gorensek et al. | 606/99 |
| 2002/0065560 A1 * | 5/2002 | Varga et al. | 623/17.16 |
| 2002/0151979 A1 * | 10/2002 | Lambrecht et al. | 623/17.16 |
| 2003/0040796 A1 * | 2/2003 | Ferree | 623/17.11 |
| 2003/0074075 A1 * | 4/2003 | Thomas et al. | 623/17.16 |
| 2003/0074076 A1 | 4/2003 | Ferree et al. | |
| 2003/0078579 A1 * | 4/2003 | Ferree | 606/53 |
| 2003/0195514 A1 * | 10/2003 | Trieu et al. | 606/61 |
| 2004/0002763 A1 * | 1/2004 | Phillips et al. | 623/17.16 |
| 2004/0002764 A1 * | 1/2004 | Gainor et al. | 623/17.16 |
| 2004/0024463 A1 * | 2/2004 | Thomas et al. | 623/17.16 |
| 2004/0210226 A1 * | 10/2004 | Trieu | 606/72 |
| 2005/0043796 A1 * | 2/2005 | Grant et al. | 623/17.11 |

(Continued)

OTHER PUBLICATIONS

International Search Report dated Jun. 26, 2008, from the International Searching Authority in corresponding International (PCT) Application No. PCT/US2007/088706.

*Primary Examiner* — Eduardo C Robert
*Assistant Examiner* — Lynnsy Schneider
(74) *Attorney, Agent, or Firm* — Fitch, Even, Tabin & Flannery

(57) ABSTRACT

An implant retention device is provided to assist in restraining movement of a nuclear implant and to assist in preventing expulsion of the nuclear implant through an incision portal or defect in the annular wall. In one form, the implant retention device comprises an expulsion prevention member associated with the nuclear implant and is configured to transition between an unexpanded position and an expanded position. In another form, a method for restraining a nuclear implant includes cutting an opening in the annulus, shifting an implant retention device into an unexpanded position, inserting the implant retention device through the opening, and shifting the retention device to an expanded position.

23 Claims, 8 Drawing Sheets

U.S. PATENT DOCUMENTS

| | | | |
|---|---|---|---|
| 2005/0043798 A1* | 2/2005 | Eckman | 623/17.11 |
| 2006/0247776 A1* | 11/2006 | Kim | 623/17.12 |
| 2006/0247784 A1* | 11/2006 | Kim | 623/17.16 |
| 2006/0253121 A1* | 11/2006 | Gorensek et al. | 606/101 |
| 2006/0253132 A1* | 11/2006 | Evans et al. | 606/151 |
| 2007/0100348 A1* | 5/2007 | Cauthen et al. | 606/99 |
| 2007/0162131 A1* | 7/2007 | Friedman et al. | 623/17.11 |
| 2007/0270961 A1* | 11/2007 | Ferguson | 623/17.11 |

* cited by examiner

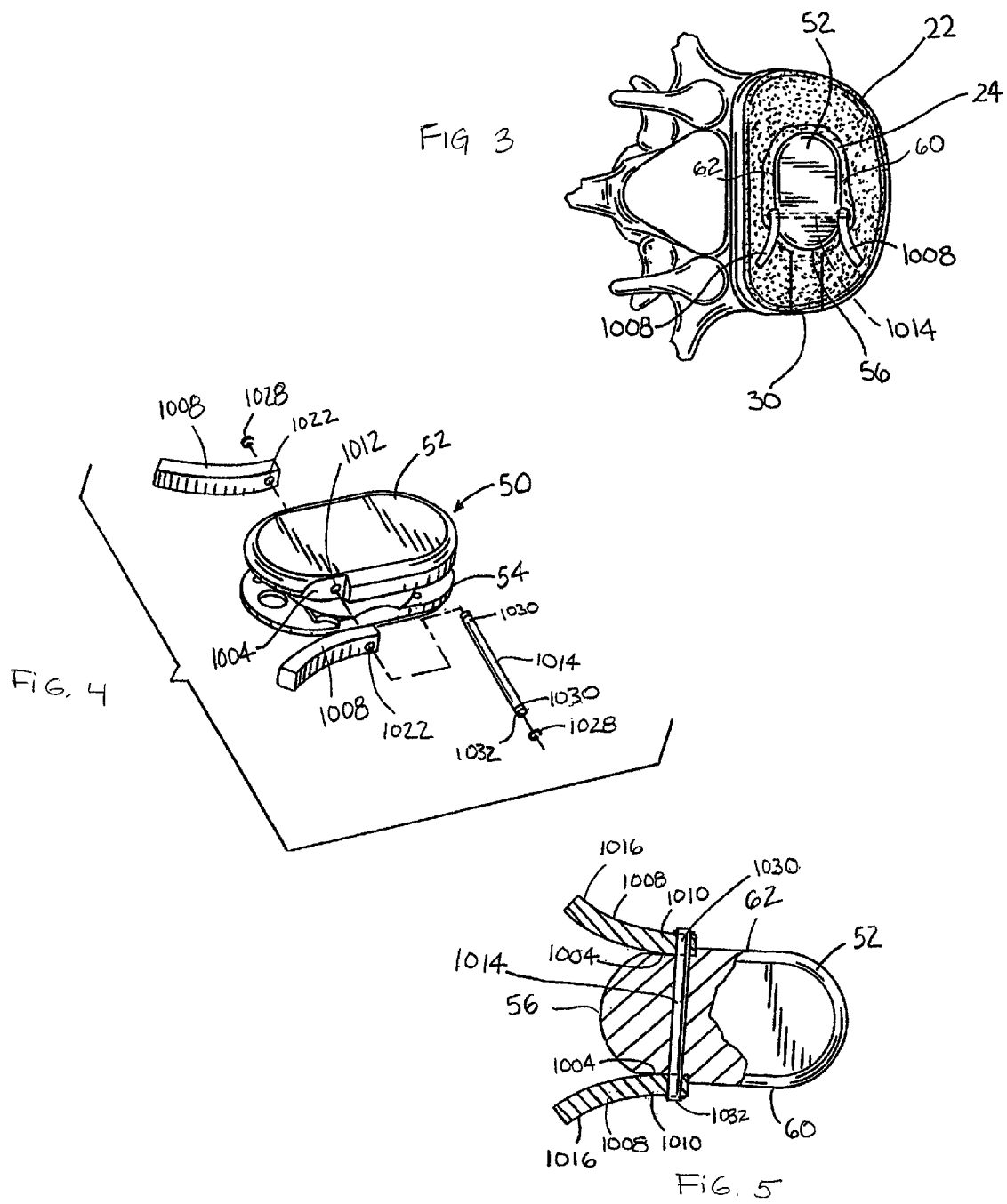

IMPLANT RETENTION DEVICE AND METHOD

CROSS REFERENCE TO RELATED APPLICATIONS

This application claims the benefit of U.S. Provisional Application No. 60/871,641, filed Dec. 22, 2006, and U.S. Provisional Application No. 60/948,273, filed Jul. 6, 2007, both of which are hereby incorporated by reference as if reproduced herein in their entirety.

FIELD OF THE INVENTION

The invention relates to artificial intervertebral implants and devices for securing and retaining the implant in an intervertebral space.

BACKGROUND OF THE INVENTION

The most common orthopedic condition for which professional medical treatment is sought is lower back pain. Although many factors may be responsible for causing lower back pain, a principal factor is damage or degeneration of an intervertebral spinal disc resulting in impingement on the nerve system, specifically the spinal cord, located within the spine. Such impingement may result in, for instance, loss of mobility, urinary and fecal incontinence, and sciatica or pain experienced in the extremities.

Damage to or degeneration of a spinal disc can result from a number of factors such as abuse or age. The disc itself is composed primarily of an annulus and a nucleus contained therein. The annulus is a fibrous annular piece that attaches to the adjacent vertebrae and contains the nucleus, which is in turn a gel-like viscous material capable of shock absorption and flowable to permit poly-axial rotation and resilient compression of the vertebrae and spine. Most frequently, disc degeneration results from damage occurring to the annulus such that the flowable nucleus material may leak or seep out of the annulus. Disc degeneration also can occur in other ways, such as by being deprived of nutrient flow leading to a dried and susceptible to damage disc. Because the nuclear material is flowable, extensive damage to the annulus is not necessary for leakage to occur.

A recent, though not new, development for spinal surgery is a procedure known as disc arthroplasty for restoring or reconstructing the disc using a prosthesis to replace a portion or entirety of the damaged disc. The primary objective of disc arthroplasty is to restore or maintain the normal disc anatomy and functions, while addressing and treating the causes of the pain.

Two types of prostheses for disc arthroplasty are currently believed to merit further development by medical science and research. One type is a total disc prosthesis, or TDP, where the entire spinal disc is replaced after radial discectomy. A typical TDP includes structures that together mimic the properties of a natural disc.

The other type is a disc nucleus prosthesis, or DNP, that is used to replace only the nucleus of a spinal disc after a nucleotomy while retaining the annulus of the disc and, possibly, the end plates intact. As discussed above, failure of the natural disc does not require extensive damage to the annulus, and the annulus would often be capable of retaining a non-flowing prosthetic nucleus. Implantation of a DNP involves clearing of the natural nucleus from the annulus through the procedure known as nucleotomy, and inserting the DNP within the annulus. Accordingly, disc nuclear prostheses (DNPs) are typically smaller and require less extensive surgery than TDPs do.

An issue related to DNPs is implant extrusion, defined as the tendencies for an implant not to remain seated, and for the implant to back out of its intended seat in the nuclear space. To prevent this, many designs for disc implants attempt to secure to the end plates of the vertebrae by providing securement features on the implant. The nuclear implants may have one or more restraining features, such as, for example, keels or other implant protrusions that seat into the bone, apertures integrated into the implant for bone in-growth such as a porous surface or coatings, or screws to screw the implant to the bone. These and other similar features restrain the implant in a predetermined orientation to the surrounding boney bodies to thereby properly support the skeletal structure and prevent damage of any soft tissues. These features, however, may violate the integrity of the end plates to a degree where revision surgery is limited. Violation of the vertebrae by the securement may cause bleeding, or calcification of the end plate, either of which can result in pain, loss of mobility, necrosis, or deterioration of any implant device.

Some arthroplasty devices are designed to float or sit unrestrained within a ligamentous joint capsule. These devices may rely purely on the soft tissue holding the replacement device in the predetermined position. An unrestrained intervertebral artificial nucleus device would benefit from an intact annulus to secure the implant in the predetermined position and prevent its expulsion into the sensitive nerve structure located just outside the annulus. The health of the annulus, however, is often compromised through the degenerative disc disease process and may not be intact. The annulus may have tears or may be poorly nourished and weak such that it cannot adequately serve by itself to restrain the nucleus replacement device within the confines of the annulus. Additionally, the annulus is typically at least partially incised during surgery to make an opening for removal of the diseased nucleus material and to serve as a window for placing the nucleus replacement device in its predetermined position. It is possible for this window to serve as an undesired expulsion portal for the nucleus implant.

For these and other reasons, the implant retention devices described herein may be utilized to assist in the retention of a nuclear implant, particularly those that do not have other restraining features, in a predetermined skeletal relationship.

SUMMARY OF THE INVENTION

In accordance with an aspect of the present invention, an implant retention device is provided to assist in restraining movement of a nuclear implant and to assist in limiting expulsion of the nuclear implant through an incision portal or defect in the annular wall. Generally, an implant is provided with an implant retention device including a movable or expandable blocking member disposed on the implant. The implant retention device has an unexpanded or compressed orientation, wherein the blocking member is not expanded, and the implant has a compact configuration or size capable of fitting through an annular wall opening. The implant retention device also has an expanded configuration, wherein the blocking member is expanded, and the implant has a second, larger contour or size, such that the implant is kept from being expelled from the nuclear space through the annular wall opening. The unexpanded orientation is intended to allow the implant to be inserted through the annular opening and into the nuclear space. Once the implant is implanted in the nuclear space, the implant retention device may be shifted to the expanded orientation, wherein the expandable member is actuated or allowed to expand. The implant contour or size when the implant retention device is in the unexpanded orientation may be slightly larger than the annular wall opening, as the opening may stretch somewhat during insertion of the implant. However, when the implant or expandable member is referred to herein as being smaller or having a span less than that of the annular opening, it is implied that the implant's or expandable member's span is less than the stretched opening. In addition, the size or contour of the implant with the retention device in the expanded orientation is configured to keep the implant from backing through the annular wall opening, despite any stretching of the opening. In effect, the surfaces of the movable or expandable member will interact with the annulus or other spinal tissues in the intervertebral space, such as a vertebral endplate, thereby interfering with movement of the implant through the annular opening. The movable or expandable member may be integrated with the implant, or may be attached separately as described below. In addition, the movable or expandable member may be made from a resilient material, such that it expands due to its own internal forces when released from a compressed position, or alternatively, the expandable member may be moved due to external forces acted thereon, such as those initiated by a surgeon or by a compressed spring.

In one embodiment, an implant device may comprise a pair of resilient prongs disposed on opposing sides of the nuclear implant. The prongs are configured to be shifted from a compressed position with a span less than the stretched opening in the annular wall to an expanded position with a span greater than the opening in the annular wall with the implant inserted through the annular wall opening to keep the implant in the nuclear space. The implant is preferably formed with an upper and lower portion, such as top and bottom shells, with the prongs optionally being disposed on either of the top or bottom shell of the implant. The prongs preferably extend beyond a trailing end of the implant toward the annular opening. By one approach, the pair of resilient prongs may be integrally formed in the implant. Alternatively, a mounting attachment may be provided that is configured to engage with the nuclear implant, wherein the resilient prongs are attached to the mounting attachment. The mounting attachment may comprise, for example, a band that engages with a corresponding groove or feature in the implant. The band may be rectilinear to engage with a rectilinear feature on the implant or may be curvilinear to surround at least a portion of the perimeter of the implant. By another approach, a pin may be inserted through a hole in the implant, with one of the pair of prongs being mounted on each end of the pin. The implant may be configured and arranged to accommodate the pair of prongs on each end of the implant.

In accordance with another aspect, a method is provided wherein an annular opening is formed in the annular wall by cutting the annular wall for insertion of a nuclear implant into a nuclear space. The implant retention device is shifted to an unexpanded position relative to the implant such that the implant and implant retention device together have a size that is insertable through the annular opening. The implant retention device is then inserted through the annular opening in the unexpanded position. The implant retention device is then shifted to an expanded position such that the implant retention device has an expanded size greater than the size of the annular opening to keep the nuclear implant from being expelled from the nuclear space through the annular opening. The implant retention device may be disposed on the nuclear implant, such as a pair of opposing resilient prongs disposed on a trailing end of the implant, wherein an unexpanded or compressed position is formed by compressing together end portions of the prongs.

BRIEF DESCRIPTION OF THE DRAWINGS

FIG. 3 is a cross-sectional top view of the spinal section of FIG. 2 taken along line 3-3 thereof and showing the nuclear implant and the implant retention device;

FIG. 4 is an exploded perspective view of the implant retention device and nuclear implant of FIG. 1;

FIG. 5 is a partial cross-sectional top view of the implant retention device and nuclear implant of FIG. 1;

DETAILED DESCRIPTION

Figure 1:
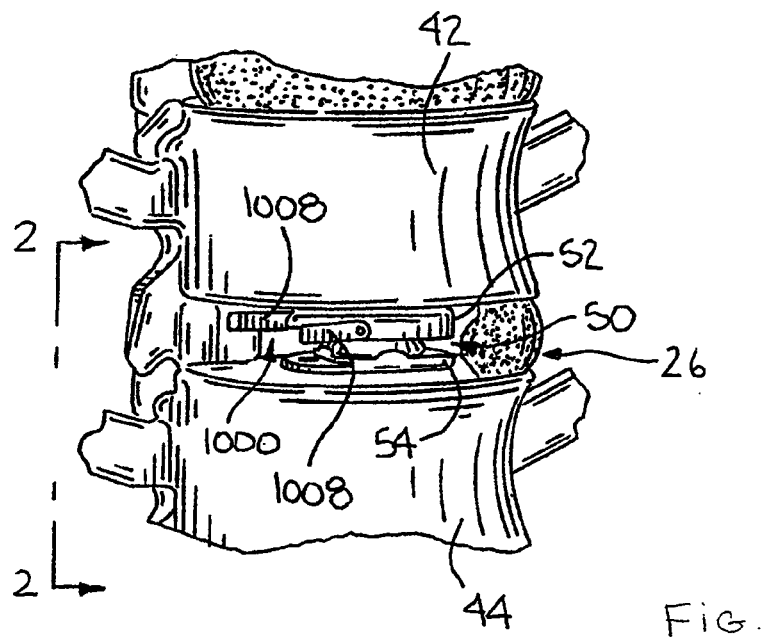
FIG. 1 is a perspective view of a first embodiment of an implant retention device secured to a nuclear implant and inserted into a nuclear space of a spinal section.
Figure 2:
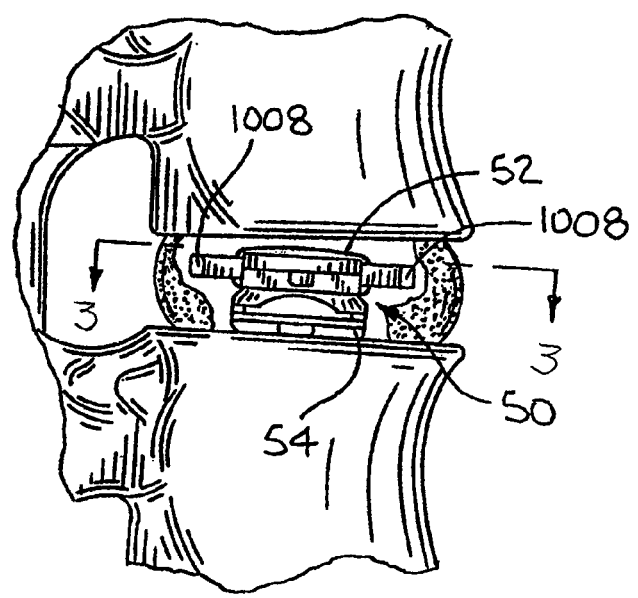
FIG. 2 is a partial side view of the implant retention device, nuclear implant, and spinal section of FIG. 1 taken along line 2-2 thereof.

Generally speaking, pursuant to these various embodiments, implant retention devices are disclosed herein, with each device directed to maintaining a nuclear implant in position within a nuclear space and limiting the implant from backing out through an opening in the annulus. It shall be understood that retention refers to retaining, restraining, controlling, or maintaining the implant within the nuclear space to limit the expulsion of the implant out of the nuclear space through the annular opening. Referring now to the drawings, and in particular to FIGS. 1-3, a first embodiment of an implant retention device 1000 is shown. A nuclear implant 50 is inserted through an annular opening 30 in the wall of the annulus 22 and positioned within a nuclear space 24 of a disc 26 located between adjacent upper vertebra 42 and lower vertebra 44. The annular opening 30 is typically created during surgery prior to implantation of the nuclear implant 50 to serve as a portal for removing the nucleus and as a surgical window for inserting the implant 50 into the nuclear space 24. However, the annular opening 30 can also be formed from a tear or weakening of the annulus 22. The annular opening 30 generally extends from the exterior of the annulus 22 through to the nuclear space 24. The implant retention device, for this and other implant retention device embodiments disclosed herein, is generally shown being used in conjunction with a nuclear implant 50 comprising a top shell 52 and a bottom shell 54. Each shell 52, 54 has a peripheral shape of an oval or racetrack shape, such that the implant has a length along a longitudinal axis and a width shorter than the length transverse to the longitudinal axis. A concave recess is formed in the top shell 52 and a corresponding dome surface is formed in the bottom shell 54, with the dome surface being received in the concave recess to allow for relative translational motion and movement between the top shell 52 and the bottom shell 54. The nuclear implant 50 shown and described herein is used as an illustrative example, with other configurations of nuclear implants or nuclear replacement devices being contemplated for use in conjunction with the implant retention devices discussed herein.

The implant retention device may be in the form of a feature or features such as a blocking member formed on or attached to the implant that prevent the expulsion of the implant from the joint capsule. For example, a nuclear implant or replacement device may be modified to include one or more resilient prongs as part of the upper or lower components of the nuclear implant. In the following embodiments utilizing the prong feature, the prongs are illustratively shown as being mounted or secured to the top shell 52 of the implant 50. It should be noted that the prong feature of the implant retention device may alternatively be incorporated into the bottom shell. By having the prongs secured to either of the top or the bottom shell, the basic function of the nuclear implant is not interfered with or impeded. The prongs are preferably mounted directly to the nuclear implant. Therefore, once the implant is inserted, movement restraint is provided without the need for an additional procedure for installation of the implant retention device.

Referring now to FIGS. 1-5, an embodiment of an implant retention device 1000 is shown having a pair of resilient arcuate prongs 1008 secured to the top shell 52 of a nuclear implant 50. The prongs 1008 may be formed of a resilient material, such as a polymer or a resilient metal, but may be made of any other known metals, ceramic, plastic, composite material, or elastomer. The prongs 1008 may be fastened or otherwise attached to one or more sides of the nuclear implant 50. The prongs 1008, as shown, are attached to each lateral side 60, 62 of the top shell 52 of the implant 50 at a point generally between the center and trailing end 56 of the implant 50. The top shell 52 of the implant 50 has a generally oval-shaped perimeter; however, indented portions 1004 may be formed in the opposing lateral sides 60, 62 of the top shell 52 perimeter to accommodate the prongs 1008, as shown in FIGS. 4 and 5. The indented portions 1004 allow an end portion 1010 of each prong 1008 to mate with the top shell 52 and sit flush thereagainst. A through hole 1012 is formed in the top shell 52, extending between the opposing indented portions 1004. A pin 1014 is inserted in the through hole 1012, with the pin 1014 sized such that mount end portions 1030 of the pin 1014 extending beyond the sides 60, 62 of the implant 50 such that each prong 1008 can be mounted onto the mount end portions 1030 of the pin 1014. Each prong 1008 has a hole 1022 therethrough at the end 1010 to receive the pin 1014. As shown, when each prong 1008 is disposed on the pin 1014, an end portion 1032 of the pin 1014 extends beyond the outer edge of each prong 1008. A snap ring 1028 or other securing mechanism (not shown) may be affixed to the exposed end of the pin 1014 to secure the 1008 prong to the top shell 52. The snap ring 1028 thus substantially prevents the prong 1008 from slipping off of the pin 1014 and maintains the prong 1008 in position against the top shell 52. The prongs 1008 are sized in length to extend beyond the trailing end 56 of the implant 50 once mounted to the implant 50. The arcuate prongs 1008 curve away from the implant 50 to give the implant 50 a greater width at the trailing end 56 thereof.

The prongs 1008 are secured adjacent the trailing end 56 of the implant 50 and positioned adjacent the annular opening 30 upon insertion of the implant 50 into the nuclear space 24. Prior to insertion of the implant 50, the resilient prongs 1008 are compressed in at the ends 1016 such that the prongs 1008 move toward each other. By compressing the prongs 1008, the ends 1016 of the prongs 1008 move inward to reduce the span of the prongs 1008 such that the prongs 1008 extend generally linearly from the implant 50 or curve in toward the implant 50. With the prongs 1008 in the compressed position, the implant 50 is then able to fit through the annular opening 30 such that the implant 50 can be inserted into the nuclear space 24. The prongs 1008 may be compressed by an insertion instrument or tool, such that the prongs 1008 are shifted from an expanded configuration to a compact configuration. Once the implant 50 is inserted, the instrument is operable to shift the prongs 1008 from a compact configuration to an expanded configuration. Alternatively, the retention device, in the form of a blocking member, may be shifted from a compact configuration to an expanded configuration by numerous other methods, such as using a temporary adhesive to hold the member in the compact configuration until after the retention device is inserted into the nuclear space 24. In another form, the blocking member may be held by a string or wire disposed thereabout, such that the retention device may be shifted to an expanded configuration simply by pulling or removing the string or wire. In yet another form, the blocking member may be formed out of a heat-activated shape memory material, such as Nitinol, such that the blocking member is in the compact configuration at room temperature, but is shifted to an expanded configuration when subjected to higher temperatures, such as body temperature.

After the implant has been inserted, the prongs 1008 are released to expand to their original position curved away from the implant 50, thus giving the implant 50 a greater width at the trailing end 56 adjacent the annular opening 30. The prongs 1008 will expand outward to a diameter or span greater than size of the annular opening 30. The implant 50 is incapable of recompressing the prongs 1008. In addition, any forces exerted on the prongs 1008 from the inner wall of the annulus 22 are incapable of recompressing the prongs 1008. If the implant 50 has forces within the nuclear space 24 to force it out towards the annular opening, the flexible prongs 1008 will stop the implant 50 from being expelled through the annular opening 30 due to the increased span of the implant 50 provided by the prongs 1008 and interference of the prongs 1008 with the inner annular wall.

By another approach, the prongs may be part of a component which snaps to the perimeter of the top shell of the implant. Referring now to FIGS. 6-10, an additional embodiment of the implant retention device 1100 is shown. In this embodiment, a pair of arcuate resilient prongs 1108 are integral with a band 1110 configured to engage with the perimeter of the top shell 52 of the implant 50. The prongs 1108 and band 1110 may be formed of a resilient material, such as a polymer or a resilient metal, but may be made of any other known metals, ceramic, plastic, composite material, or elastomer. The band 1110 includes a linear portion 1112 that extends between the pair of prongs 1008, with the linear portion 1112 fitting into a groove 1120 on the underside 64 of the top shell 52 of the implant 50. The linear portion 1112 extends across the width of the underside 64 of the top shell 52 of the implant 50 at a point generally between the center and trailing end 56 of the implant 50. The band 1110 further includes a curvilinear portion 1140 that continues from one end 1124 of the linear portion 1112 and extends around the outer perimeter of a portion of the top shell 52 to the other end 1126 of the linear portion 1112. The curvilinear portion 1140 preferably extends around approximately two-thirds of the perimeter of the top shell 52, including the leading end 58 of the implant 50, following the oval-shaped contour of the top shell 52 of the implant 50.

Figure 6:
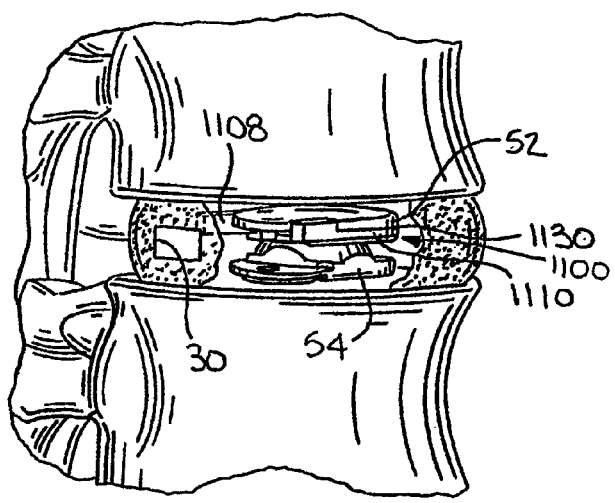
FIG. 6 is a perspective view of a second embodiment of an implant retention device secured to a nuclear implant and inserted into a nuclear space of a spinal section.
Figure 7:
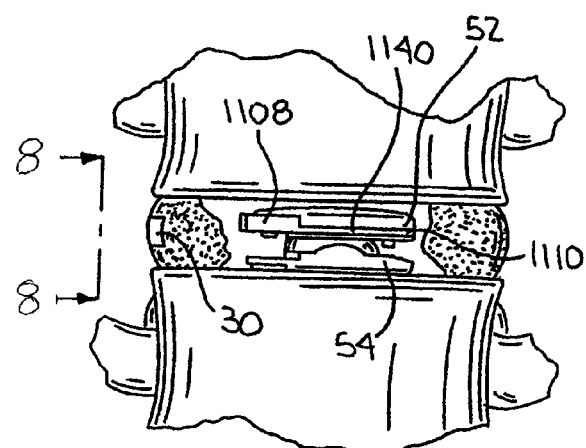
FIG. 7 is a partial front view of the implant retention device, nuclear implant, and spinal section of FIG. 6.
Figure 8:
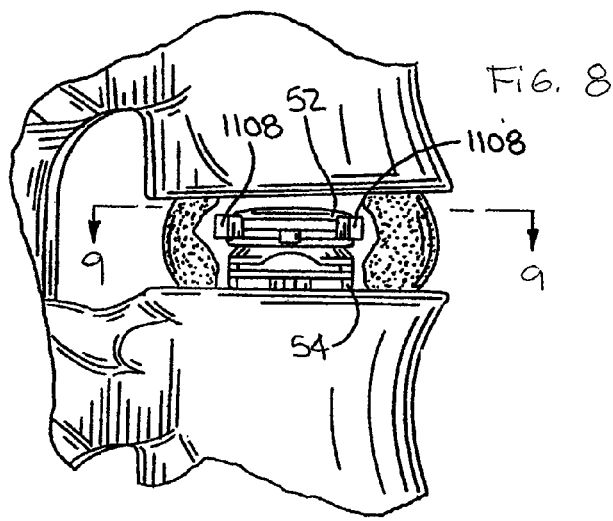
FIG. 8 is a partial side view of the implant retention device, nuclear implant, and spinal section of FIG. 7 along line 8-8 thereof.
Figure 9:
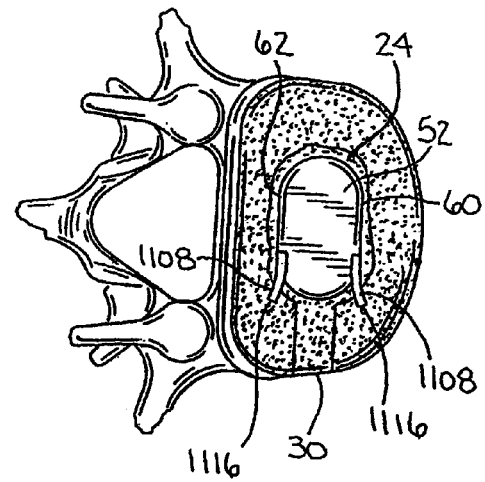
FIG. 9 is a cross-sectional top view of spinal section of FIG. 8 along line 9-9 thereof and showing the implant retention device and nuclear implant.
Figure 10:
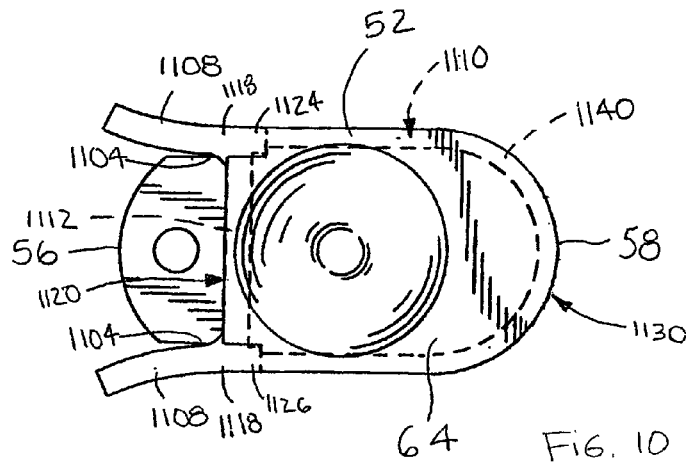
FIG. 10 is a bottom view of a top shell of the nuclear implant of FIG. 6 showing the implant retention device secured thereto.
Figure 11:
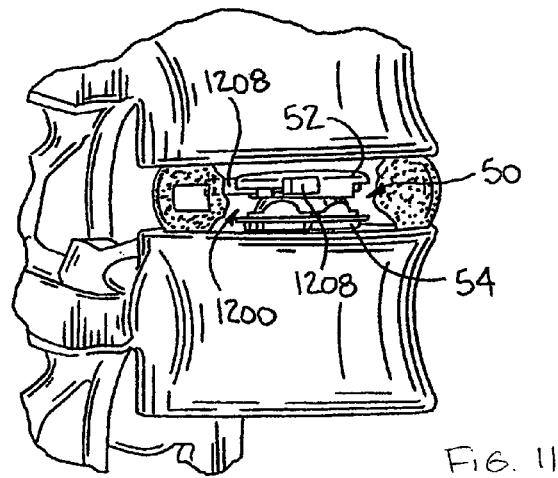
FIG. 11 is a perspective view of a third embodiment of an implant retention device secured to a nuclear implant and inserted into a nuclear space of a spinal section.
Figure 12:
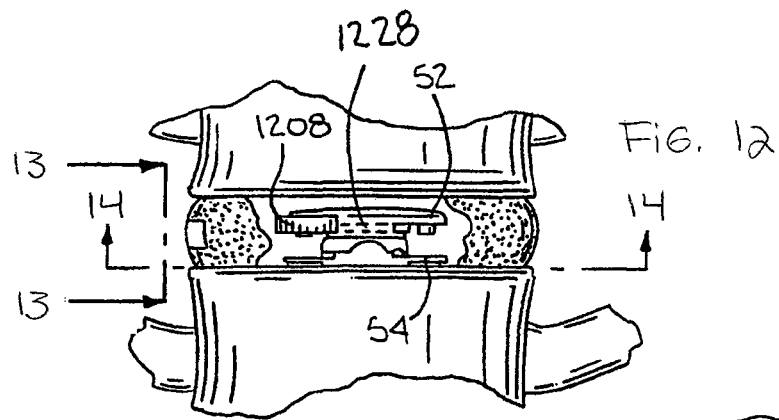
FIG. 12 is a partial front view of the implant retention device, nuclear implant, and spinal section of FIG. 11.
Figure 15:
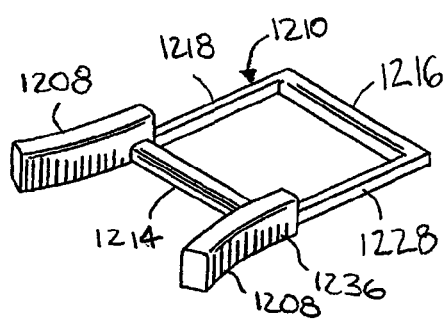
FIG. 15 is a perspective view of the implant retention device of FIG. 11.
Figure 13:
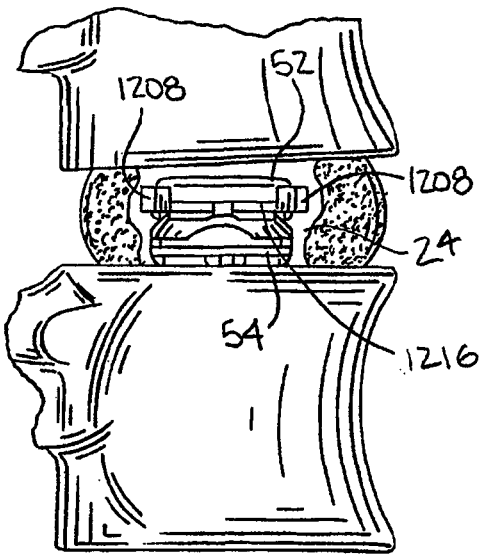
FIG. 13 is a partial side view of the implant retention device, nuclear implant, and spinal section of FIG. 12 along line 13-13 thereof.
Figure 14:
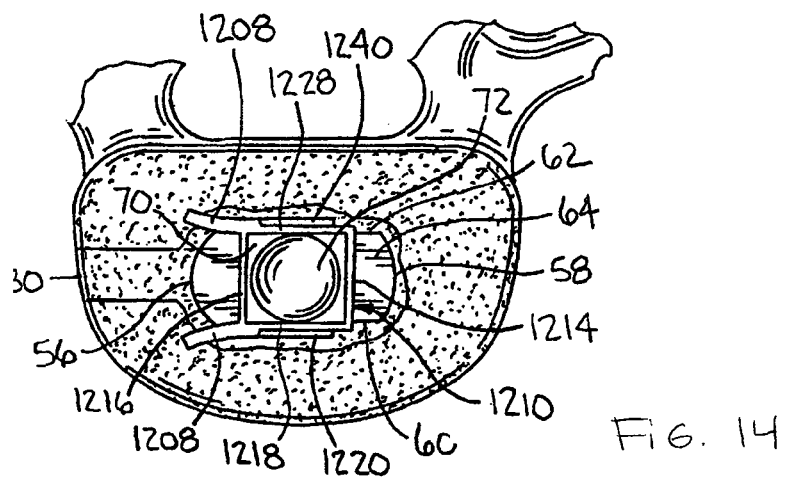
FIG. 14 is a cross-sectional bottom view of the spinal section and a top shell of the nuclear implant of FIG. 12 along line 14-14 thereof and showing the implant retention device secured thereto.
Figure 16:
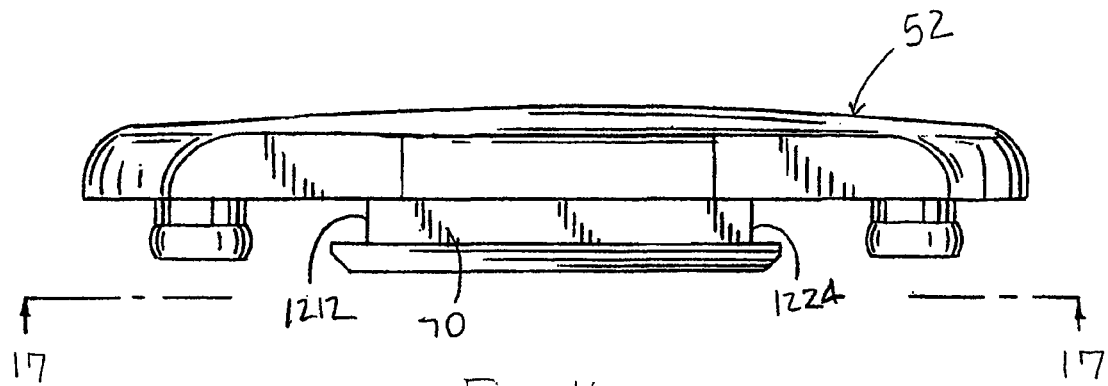
FIG. 16 is a side view of the top shell of the nuclear implant of FIG. 12.
Figure 17:
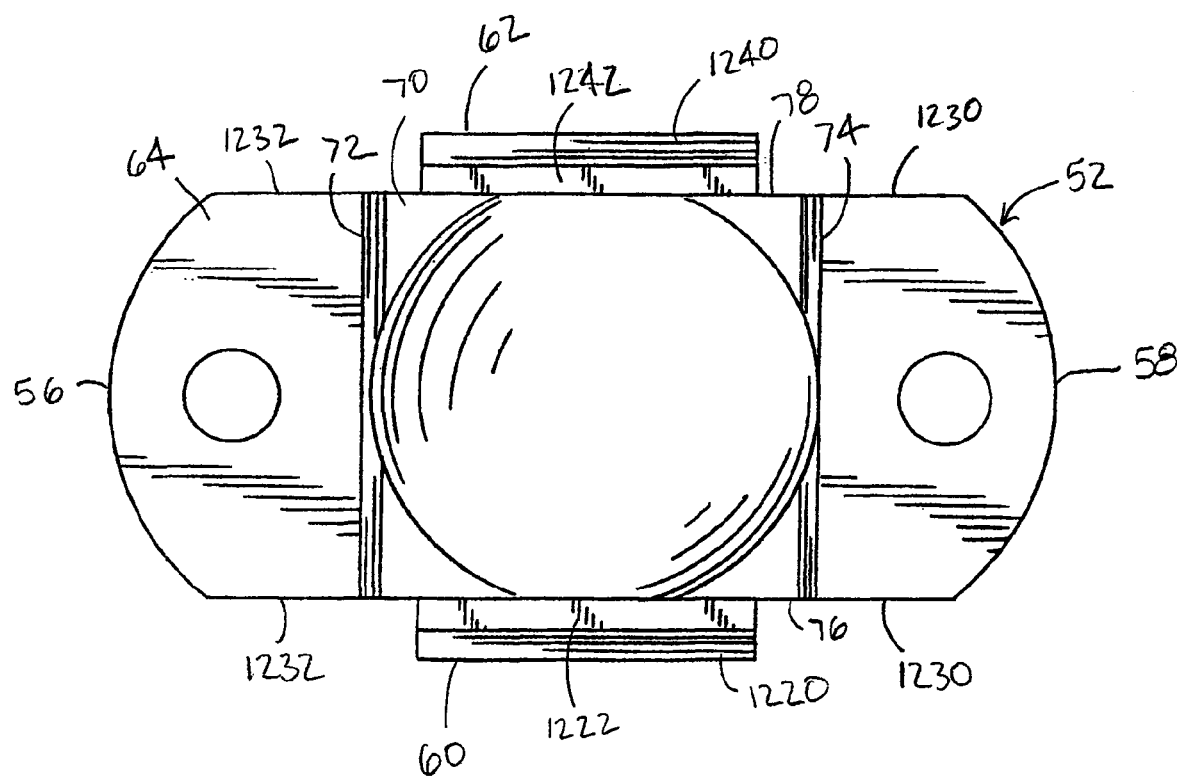
FIG. 17 is a bottom view of the top shell of the nuclear implant of FIG. 16 taken along line 17-17 thereof.
Figure 18:
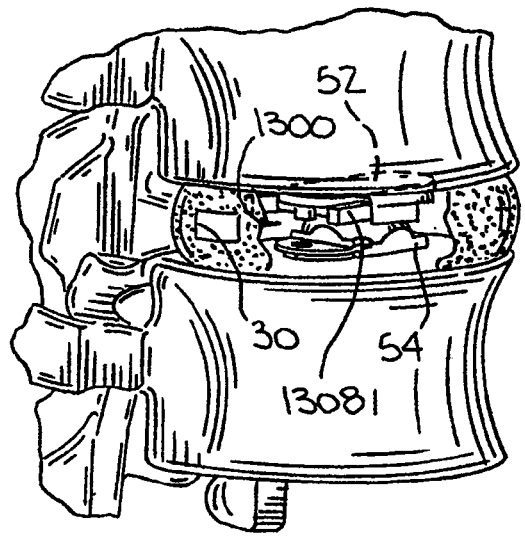
FIG. 18 is a perspective view of a fourth embodiment of an implant retention device secured to a nuclear implant and inserted into a nuclear space of a spinal section.
Figure 19:
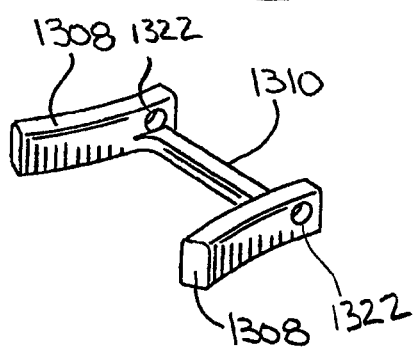
FIG. 19 is a perspective view of the implant retention device of FIG. 18.
Figure 20:
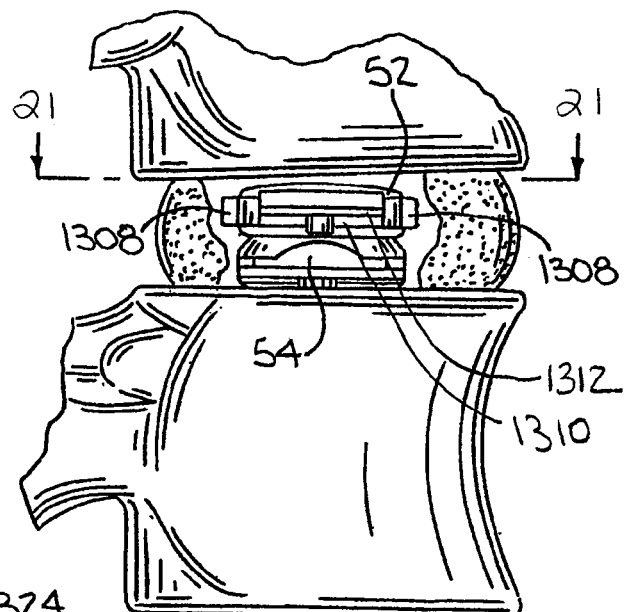
FIG. 20 is a partial side view of the implant retention device, nuclear implant, and spinal section of FIG. 18.
Figure 21:
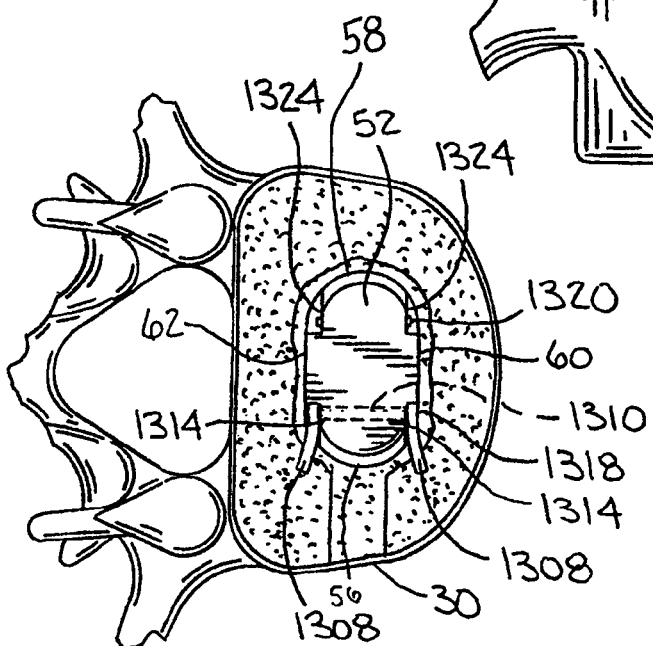
FIG. 21 is cross-sectional top view of spinal section of FIG. 20 along line 21-21 thereof and showing the nuclear implant with the implant retention device attached thereto.

A perimeter groove 1130 is formed around a portion of the perimeter of the top shell 52 to accommodate the curvilinear portion 1140 of the band 1110. The curvilinear portion 1140 nests in the groove 1130 such that the curvilinear portion 1140 preferably does not extend beyond the lateral sides 60, 62 of the top shell 52. Preferably, opposing indentations 1104 are formed in the top shell 52 to accommodate the prongs 1108 of the implant retention device 1100. The indentations 1104 receive an end 1118 of the prong 1108 such that the prong 1108 mates with the top shell 52 and the end 1118 of the prong 1108 sits flush against an exterior surface of the top shell 52. As shown in FIG. 6, the prongs 1108 curve away from the implant 50 and have a greater height than the curvilinear portion 1140 and linear portion 1112 of the band 1110. The prongs 1108 are sized to extend beyond the trailing end 52 of the implant 50 once mounted to the implant 50. Prior to insertion of the implant 50, the resilient prongs 1108 are compressed in at the ends 1116 such that the prongs 1008 move toward each other to reduce the span of the prongs 1108 such that the implant 50 can be inserted through the annular opening 30. Upon insertion, the prongs 1108 extend from the trailing end 56 of the implant 50 toward the annular opening 30. When the prongs 1108 are released from the compressed position, the prongs 1108 have a span greater than the size of the annular opening 30 to prevent the implant 50 from being expelled through the annular opening 30. Again, any forces exerted on the prongs 1108 from the inner wall of the annulus 22 are incapable of recompressing the prongs 1108.

By another approach, the resilient prongs may be part of a component which snaps onto an underside of the top shell. Referring now to FIGS. 11-17, such an embodiment is shown. The implant retention device 1200 is generally comprised of a pair of opposed prongs 1208 that are integral with a generally rectilinear band 1210, with the band 1210 snapping around a corresponding rectilinear feature 70 on the underside 64 of the top shell 52. The prongs 1208 and band 1210 may be formed of a resilient material, such as a polymer or a resilient metal, but may be made of any other known metals, ceramic, plastic, composite material, or elastomer.

The concave recess 72 on the underside 64 of the top shell 52 is formed within a generally rectilinear projection 70 from the underside 64 of the top shell 52. The rectilinear projection 70 includes grooves 1212, 1224 on opposing sides 72, 74 to retain opposing sides 1214, 1216 of the rectilinear band 1210. The other pair of opposing sides 1218, 1228 of the band 1210 are positioned within a groove 1222, 1242 formed between an edge 76, 78 of the rectilinear projection 70 and opposing ridges 1220, 1240 extending along the lateral sides 60, 62 of the top shell 52. The lateral sides 60, 62 of the top shell 52 have a pair of opposing indentations on either side of the opposing ridges 1220, 1240, with a first pair of opposing indentations 1230 adjacent the leading end 58 of the implant 50 and a second pair of opposing indentations 1232 adjacent the trailing end 56 of the implant 50. The indentations 1230, 1232 accommodate the prongs 1208, such that exterior surfaces of the end portion 1236 of the prongs 1208 are secured in mating contact against the indentation portion 1230, 1232 of the top shell 52. When the band 1210 is snapped into the grooves 1212, 1224, 1222, 1242, the prongs 1208 are positioned along opposing lateral sides 60, 62 of the top shell 52 and extend beyond the trailing end 56 of the implant 50. The arcuate prongs 1208 are positioned such that they curve away from each other and have a span greater than the width of the annular opening 30 to prevent the implant 50 from backing out of the nuclear space 24. Again, the prongs 1208 are resilient such that they can be compressed to reduce the span for insertion through the annular opening 30 and into the nuclear space 24. The prongs 1208 are then released and allowed to expand to a span greater than the span of the annular opening 30 such that the implant is not expelled through the annular opening 30. In this embodiment, the top shell 52, including the features used to accommodate and secure the band 1210 and prongs 1208, is preferably symmetrical, such that the band 1210 may be secured with the prongs 1208 positioned on either end of the implant 50. As a result, the surgeon may attach the prongs 1208 to either end of the implant 50, depending on the side of surgical approach.

Referring now to FIGS. 18-21, another embodiment is shown in which the prongs may be secured to either of the lateral ends of the implant, with each end of the implant being configured to receive the resilient prongs. The implant retention device 1300 includes a linear portion 1310 extending between a pair of opposed prongs 1308. The prongs 1308 and linear portion 1310 may be formed of a resilient material, such as a polymer or a resilient metal, but may be made of any other known metals, ceramic, plastic, composite material, or elastomer. A groove 1312 is formed on the underside 64 of the top shell 52 adjacent the trailing end 56 for receiving and retaining the linear portion 1310, with the prongs 1308 extending past the trailing end 56 of the implant 50. The linear portion 1310 extends across the width of the underside 64 of the top shell 52 and snaps into one of the grooves 1312 to secure the implant retention device 1300. An identical groove (not shown) is formed on the underside 64 of the top shell 52 adjacent the leading end 52 for receiving the linear portion 1310, such that the prongs 1308 can alternatively extend past the leading end 52 of the implant 50. The top shell 52, including the features used to accommodate and secure the linear portion 1310 and prongs 1308, is symmetrical, such that the linear portion 1310 may be secured in either groove, with the prongs 1308 positioned on either end of the implant 50. Although the implant retention device 1300 is shown mounted in groove 1312, it is understood that the groove on the other side of the implant 50 may be utilized such that the prongs 1308 may attach to either end of the implant 50 depending on the side of surgical approach. The prongs 1308 are integrally formed with the linear portion 1310, such that when the linear portion 1310 is secured in the groove 1312 the prongs 1308 are positioned on opposing sides 60, 62 of the top shell 52, with the prongs 1308 adjacent the annular opening 30 and extending beyond the trailing end 56 of the implant 50. Each prong 1308 has a through hole 1322 on the end 1318 adjacent the top shell 52, with a corresponding receiving projection 1320 integral with the top shell 52 to facilitate attachment of the prongs 1308 to the top shell 52. As shown, the receiving projections 1320 are located on indented portions 1314, 1324 in the lateral sides 60, 62 of the outer oval-shaped perimeter of the top shell 52 implant 50. The top shell 52 includes two pairs of opposing indented portions 1314, 1324, with a first pair of opposing indented portions 1314 located adjacent the leading end 58 of the implant and a second pair of opposing indented portions 1324 located adjacent the trailing end 56 of the implant. A receiving projection 1320 projects from the outer side surface of each of the pairs of indentations 1314, 1324. The arcuate resilient prongs 1308 curve away from the implant 50 and have an uncompressed span greater than the span of the annular opening 30. The prongs 1308 are then compressed for insertion of the implant 50 through the annular opening 30 and then allowed to expand within the nuclear space 24 to prevent the implant 50 from being expelled through the annular opening 30.

Figure 22:
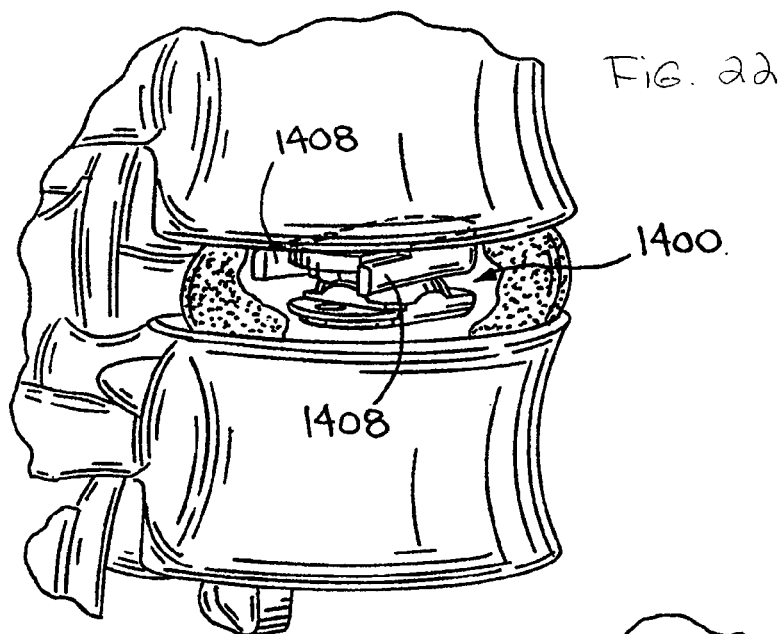
FIG. 22 is a perspective view of a fifth embodiment of an implant retention device secured to a nuclear implant and inserted into the nuclear space of a spinal section.
Figure 23:
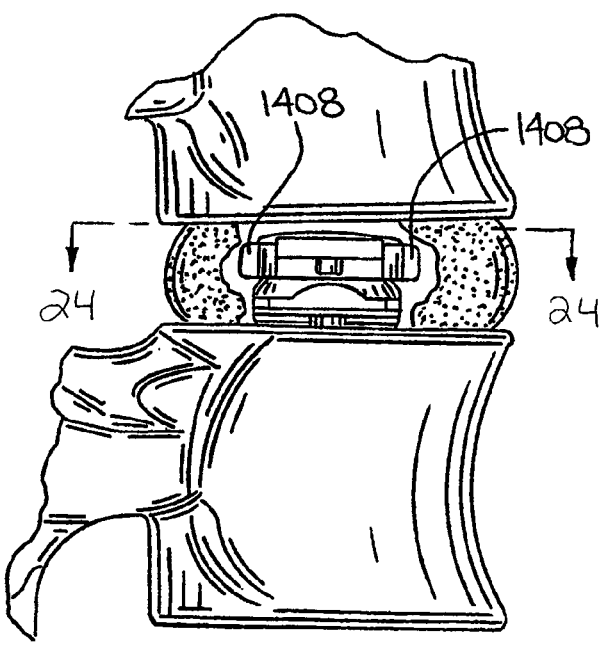
FIG. 23 is a partial left side view of the implant retention device, nuclear implant, and spinal section of FIG. 22.
Figure 24:
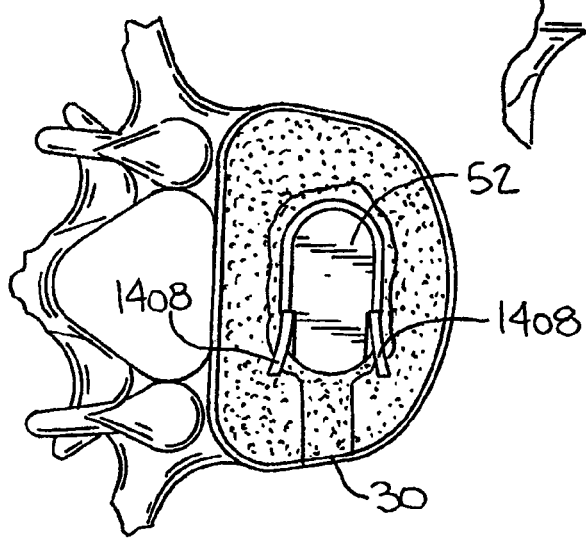
FIG. 24 is a cross-sectional top view of the spinal section of FIG. 23 along line 24-24 thereof and showing the nuclear implant and implant retention device attached thereto.

As a further embodiment of an implant restraint device 1400, resilient prongs 1408 may be machined into a shell of the implant, such that the prongs 1408 are integral with the body of the implant 50. Referring now to FIGS. 22-24, the prongs 1408 are located in generally the same location as the above-described embodiments. Again, the prongs 1408 extend beyond the trailing end 56 of the implant 50 toward the annular opening 30, the prongs 1408 having a span wider than the width of the annular opening 30 to substantially prevent any backout of the implant 50 through the annular opening 30. The prongs 1408 are integral with the top shell 52 of the implant, rather than being formed from an additional component, such as described in the above embodiments. The prongs 1408 are generally formed from the same material as the implant 50, and may be manufactured from any known metals, ceramic, plastic, composite material, or elastomer.

The implant retention devices and features as described herein may be adapted for use with a variety of artificial joint arrangements other than nuclear implants. In addition, the implant retention devices and features as described herein may be adapted for use with a variety of surgical approaches. Most of the surgical approaches shown in the illustrations are from an anterior or lateral approach but are easily adaptable for a posterior approach, for example. In a posterior approach, an incision portal is made in the posterior annulus.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. An implant device for replacing a nucleus of a natural intervertebral disc, the implant device comprising:
    a nuclear implant for being inserted through an opening in an annular wall of the natural intervertebral disc and into a nuclear space;
    upper and lower shells of the implant each comprising a body having a width thereacross; inner facing surfaces of the upper and lower shells each comprising bearing surface portions that engage with one another to provide a bearing interface between the shells such that the upper and lower shells are allowed to articulate with respect to one another;
    an elongate through hole formed in one of the shells extending across the width thereof; and
    a pair of blocking members each having a fixed portion that is connected at a respective side of the one shell body via an elongate pin disposed in the elongate through hole such that the blocking members are disposed on either end of the elongate pin and are spaced from each other at a predetermined distance across the one shell body corresponding to the width of the shell body with the pair of blocking members being shiftable between first and second orientations thereof for passing through the annular wall opening so that the implant has a compact configuration sized to fit through the annular wall opening with the blocking members shifted to the first orientation from the second orientation thereof, and an expanded configuration sized such that the implant is kept from being expelled from the nuclear space through the annular wall opening after insertion of the implant by interference between the blocking members shifted from the first orientation to the second orientation thereof and the annular wall.

2. The implant device of claim 1, wherein the implant has a lateral width including the width of the implant shell body transverse to a longitudinal axis of the implant, wherein the lateral width of the implant is greater when the blocking members are in the second orientation.

3. The implant device of claim 1, wherein the implant has a trailing end opposite an insertion end, and the blocking members are disposed adjacent to the trailing end.

4. The implant device of claim 1, wherein the blocking members are configured to be moved from the first orientation to the second orientation by a tool.

5. The implant device of claim 1, wherein each blocking member comprises a resilient prong disposed on the one implant shell body wherein the first orientation is a resiliently flexed position to fit through the annular wall opening, and the second orientation is an unflexed position to keep the implant from being expelled from the nuclear space through the annular wall opening.

6. The implant device of claim 5 wherein each resilient prong has an arcuate shape and is attached to the elongate pin at one end of the resilient prong.

7. The implant device of claim 5 wherein each prong is disposed on the upper shell body.

8. The implant device of claim 7, wherein:
    the bearing interface between the upper and lower rigid shells comprises a protrusion and a corresponding recess in mating engagement with each other such that the lower shell is kept from being expelled from the nuclear space through the annular opening via interference between the protrusion and recess.

9. The implant of claim 8, wherein the protrusion has a convex dome-shaped configuration and the corresponding recess has a corresponding concave configuration such that the protrusion and recess may slide with respect to one another allowing for polyaxial articulation between the upper and lower shells.

10. The implant device of claim 5 wherein each prong is disposed on the lower shell body.

11. The implant device of claim 5 wherein each prong extends beyond a trailing end of the implant toward the annular opening.

12. The implant device of claim 1, wherein the blocking members comprise a pair of resilient prongs, wherein the compact configuration is a compressed position, wherein the prongs are sized to fit through the annular wall opening, and the expanded configuration is an uncompressed position, wherein the prongs interfere with the annular wall to keep the implant from being expelled from the nuclear space through the annular wall opening.

13. A method for restraining a motion-preserving nuclear implant against expulsion from a nuclear space within an annulus, the method comprising:
   providing an articulating nuclear implant comprising upper and lower shells each having a width and a length along a longitudinal axis longer than the width and an articulating bearing interface between the shells, one of the shells including a pair of blocking members having fixed portions connected to either side of the one implant shell via an elongate pin disposed in an elongate through hole of the one implant shell such that the blocking members are disposed on either end of the elongate pin and are spaced from each other at a predetermined distance across the one implant shell corresponding to the width thereof;
   cutting an opening in an annular wall to form an annular opening for insertion of the nuclear implant into the nuclear space;
   shifting the blocking members to an unexpanded position relative to the implant such that the implant and blocking members together have a size that is insertable through the annular opening;
   inserting the upper and lower shells and the blocking members through the annular opening into the nuclear space surrounded by the annulus in the unexpanded position;
   orienting the shell bodies in the nuclear space within the annulus with the longitudinal axis of the shells generally aligned with a lateral axis of the nuclear space; and
   shifting the blocking members to an expanded position relative to the implant such that the blocking members have an expanded size greater than the size of the annular opening to keep the nuclear implant from being expelled from the nuclear space through the annular opening.

14. The method of claim 13 wherein shifting the blocking members to an unexpanded position comprises shifting the blocking members laterally with respect to the implant.

15. The method of claim 13 wherein shifting the blocking members to an unexpanded position includes flexing resilient members toward the implant.

16. The method of claim 13 wherein the blocking members are shifted to an unexpanded position by using a tool.

17. The method of claim 13 wherein shifting the blocking members to an expanded position comprises releasing resilient blocking members held in a flexed configuration.

18. A prosthetic spinal nucleus device for replacing a nucleus of a spinal disc between adjacent vertebrae, the device comprising:
   upper and lower shells sized to fit within the natural annulus of the spinal disc;
   outer surfaces of the upper and lower shells configured for engagement with inner facing surfaces of the adjacent vertebrae; inner facing surfaces of the upper and lower shells that face one another;
   sides of the upper and lower shells that extend between the outer surfaces and inner facing surfaces that define a height;
   a protrusion disposed on one of the upper and lower shells; a recess configured to mate with the protrusion disposed on the other of the upper and lower shells, wherein interference between the protrusion and mating recess keep the upper and lower shells generally in relative vertical alignment; and
   a pair of blocking members having fixed portions connected to either side of one of the upper and lower shells via an elongate pin disposed in an elongate through hole of the one implant shell such that the blocking members are disposed on either end of the elongate pin and are spaced from each other at a distance corresponding to a width of the one shell, the blocking members being shiftable between first and second orientations thereof for passing through an annular wall opening so that the device has a compact configuration sized to fit through the annular wall opening with the blocking members shifted to the first orientation from the second orientation thereof, and an expanded configuration sized such that the device is kept from being expelled from the nuclear space through the annular wall opening after insertion of the device by interference between the blocking members shifted from the first orientation to the second orientation thereof and the annular wall.

19. The nucleus device of claim 18, wherein the blocking members each comprise a resilient prong disposed on the nucleus device wherein the first orientation is a resiliently flexed position to fit through the annular wall opening, and the second orientation is an unflexed position to keep the implant from being expelled from the nuclear space through the annular wall opening.

20. The nucleus device of claim 19, wherein the resilient prong has an arcuate shape and is disposed on the upper shell.

21. The nucleus device of claim 19, further comprising an indented portion disposed on the side of the one shell for receiving an end of the resilient prong.

22. The nucleus device of claim 18, wherein the blocking members are in the form of resilient prongs disposed on the one of the shells.

23. The nucleus device of claim 22, wherein the device has a
   lateral width transverse to a longitudinal axis thereof and the resilient prongs are disposed on the upper shell and extend generally laterally away therefrom such that the lateral width of the device is greater when the prongs are in the second expanded orientation thereof.

* * * * *

UNITED STATES PATENT AND TRADEMARK OFFICE
CERTIFICATE OF CORRECTION

PATENT NO. : 8,114,160 B2  
APPLICATION NO. : 11/963496  
DATED : February 14, 2012  
INVENTOR(S) : Brian P. Janowski et al.

Page 1 of 2

It is certified that error appears in the above-identified patent and that said Letters Patent is hereby corrected as shown below:

In Claim 1, Column 10, Lines 7-13, delete the following:

"~~upper and lower shells of the implant each comprising a body having a width thereacross; inner facing surfaces of the upper and lower shells each comprising bearing surface portions that engage with one another to provide a bearing interface between the shells such that the upper and lower shells are allowed to articulate with respect to one another;~~"

In Claim 1, Column 10, Lines 7-13, insert the following:

--upper and lower shells of the implant each comprising a body having a width thereacross;
inner facing surfaces of the upper and lower shells each comprising bearing surface portions that engage with one another to provide a bearing interface between the shells such that the upper and lower shells are allowed to articulate with respect to one another;--

In Claim 18, Column 12, Lines 6-9, delete the following:

"~~outer surfaces of the upper and lower shells configured for engagement with inner facing surfaces of the adjacent vertebrae; inner facing surfaces of the upper and lower shells that face one another;~~"

In Claim 18, Column 12, Lines 6-9, insert the following:

--outer surfaces of the upper and lower shells configured for engagement with inner facing surfaces of the adjacent vertebrae;
inner facing surfaces of the upper and lower shells that face one another;--

Signed and Sealed this
Eighteenth Day of December, 2012

David J. Kappos
*Director of the United States Patent and Trademark Office*

CERTIFICATE OF CORRECTION (continued)
U.S. Pat. No. 8,114,160 B2

In Claim 18, Column 12, Lines 13-18, delete the following:

"~~a protrusion disposed on one of the upper and lower shells;~~
~~a recess configured to mate with the protrusion disposed on the other of the upper and lower shells,~~
~~wherein interference between the protrusion and mating recess keep the upper and lower shells~~
~~generally in relative vertical alignment; and~~"

In Claim 18, Column 12, Lines 13-18, insert the following:

--a protrusion disposed on one of the upper and lower shells;
a recess configured to mate with the protrusion disposed on the other of the upper and lower shells, wherein interference between the protrusion and mating recess keep the upper and lower shells generally in relative vertical alignment; and--

In Claim 23, Column 12, Lines 51-57, delete the following:

"~~The nucleus device of claim 22, wherein the device has a~~
~~lateral width transverse to a longitudinal axis thereof and the resilient prongs are disposed on the upper shell and extend generally laterally away therefrom such that the lateral width of the device is greater when the prongs are in the second expanded orientation thereof.~~"

In Claim 23, Column 12, Lines 51-57, insert the following:

--The nucleus device of claim 22, wherein the device has a lateral width transverse to a longitudinal axis thereof and the resilient prongs are disposed on the upper shell and extend generally laterally away therefrom such that the lateral width of the device is greater when the prongs are in the second expanded orientation thereof.--